United States Patent
Oki et al.

(10) Patent No.: US 7,732,582 B2
(45) Date of Patent: Jun. 8, 2010

(54) BENZONAPHTHACENE GLYCOSIDE DERIVATIVE AND USE THEREOF

(75) Inventors: Toshikazu Oki, Yokohama (JP); Yasuhiro Igarashi, Toyama (JP); Tamotsu Furumai, Yokohama (JP)

(73) Assignee: FUJIFILM Corporation, Tokyo (JP)

( * ) Notice: Subject to any disclaimer, the term of this patent is extended or adjusted under 35 U.S.C. 154(b) by 463 days.

(21) Appl. No.: 11/661,938

(22) PCT Filed: Sep. 5, 2005

(86) PCT No.: PCT/JP2005/016673

§ 371 (c)(1),
(2), (4) Date: Jul. 25, 2007

(87) PCT Pub. No.: WO2006/028229

PCT Pub. Date: Mar. 16, 2006

(65) Prior Publication Data

US 2008/0027144 A1 Jan. 31, 2008

(30) Foreign Application Priority Data

Sep. 6, 2004 (JP) .............................. 2004-258886

(51) Int. Cl.
*C07H 15/24* (2006.01)
*A01N 43/16* (2006.01)
(52) U.S. Cl. .................. 536/18.1; 536/16.8; 514/33
(58) Field of Classification Search ................ 536/18.1, 536/16.8; 514/33
See application file for complete search history.

(56) References Cited

FOREIGN PATENT DOCUMENTS

JP 2000-1497 A 1/2000

OTHER PUBLICATIONS

Berge et al. Journal of Pharmaceutical Science, 1977, 66(1), p. 1-19.*
Ueki et al. Journal of Antibiotics, 1993, 46(3), p. 455-464.*
Toshikazu Oki, Protein, Nucleic acid and Enzyme, May 1994, vol. 39, No. 6, pp. 973-978.
Karlowsky, J. A. et al., In Vitro Antifungal Activity of BMS-181184 against Systemic Isolates of Canada, Cryptococcus, and Blastomyces Species, Diagnostic Microbiology and Infectious Disease, 1997, vol. 28, No. 4, pp. 179 to 182.
Aburaki et al., The Journal of Antibiotics, Apr. 1993, vol. 46, No. 4, pp. 631-640.

* cited by examiner

*Primary Examiner*—Shaojia Anna Jiang
*Assistant Examiner*—Jonathan S Lau
(74) *Attorney, Agent, or Firm*—Birch, Stewart, Kolasch & Birch, LLP

(57) ABSTRACT

A dicarboxylic acid compound obtainable by oxidative degradation of pradimicin antibiotics, which are antibiotics consisting of the benzonaphthacene skeleton, a D-amino acid side chain and a sugar chain, for the second saccharide residue of the sugar chain, and use thereof utilizing a specific microorganism binding property thereof are provided. The dicarboxylic acid compound has significantly improved water-solubility compared with the raw material antibiotics, whilst maintaining the specific microorganism binding property.

8 Claims, No Drawings

BENZONAPHTHACENE GLYCOSIDE DERIVATIVE AND USE THEREOF

TECHNICAL FIELD

The present invention relates to a novel derivative of a compound comprising the benzonaphthacene skeleton, a D-amino acid side chain, and a sugar chain (also referred to as "benzonaphthacene glycoside") and particular use of said derivative utilizing a specific binding property between said derivative and a microorganism expressing a mannose sugar chain.

BACKGROUND ART

Among benzonaphthacene glycosides, for example, some of pradimicin antibiotics and semi-synthesized derivatives thereof bind to cells as targets that express mannan having D-mannose residues on cell surface layers, and have been considered promising, for example, as candidate compounds for antifungal agents. Reviews are available which summarize the correlation between the structures and antimicrobial activity of these compounds (see, for example, Non-patent document 1 mentioned below). Among variety of homologues or derivatives thereof, BMY-28864 (or N,N'-dimethylpradimicin FA-2) has been reported as a semi-synthesized derivative having superior water solubility and potent antimicrobial activity (see, for example, Non-patent document 2 mentioned below). Furthermore, pradimicin T1 comprising the benzo[α]naphthacenequinone skeleton bound with D-xylose at the 11-position has also been reported (see, for example, Non-patent documents 3 and 4 mentioned below).

However, any development of these compounds as medicaments has not yet been succeeded to date. Major presumable reasons include, for example:

i) these compounds have high self-aggregational property and therefore likely incorporate impurities in a culture medium (lipopolysaccharides and the like), and such impurities may possibly exhibit toxicity;

ii) solubilities of compounds as candidates for development in biological fluids (blood and the like) are still far from satisfactory, which results in insufficient kinetics in vivo such as poor absorption or clearance.

[Non-patent document 1] Oki, et al., Exp. Opin. Ther. Patents, 4(12):1483-1491 (1994)

[Non-patent document 2] Oki, et al., J. Antibiotics, 43, 1230-1235 (1990)

[Non-patent document 3] Furumai et al., J. Antibiotics, 46, 589-597 (1993)

[Non-patent document 4] Hasegawa et al., J. Antibiotics, 46, 598-605 (1993)

DISCLOSURE OF THE INVENTION

Medicaments and others comprising benzonaphthacene glycosides have not been successfully developed so far. Benzonaphthacene glycosides selectively bind to fungi expressing mannan on cell surface layers, which generally does not exist on surface layers of normal animal cells. Therefore, if a system that can effectively utilize the cell selectivity can be obtained, the system will be useful in technical fields of therapeutic and diagnostic agents and the like, and also useful as a tool for basic researches. Further, benzonaphthacene glycosides have a property of recognizing and binding to mannose, and accordingly, can recognize microorganisms expressing a mannose sugar chain, especially a high mannose sugar chain, on the surface layer, as well as fungi (for example, animal and plant cells (including insect cells), fungi and viruses). Therefore, if the benzonaphthacene glycosides are conjugated with an anti-HIV (human immunodeficiency virus) agent or an antifungal agent, they can be utilized for targeting (or drug delivery) for transporting a medicament to such cells and viruses, or if the benzonaphthacene glycosides are conjugated with a fluorescent compound or biotin, they can be utilized for labeling (staining) of cells or viruses expressing a high mannose sugar chain in vivo. Furthermore, if these benzonaphthacene glycosides are immobilized on a solid phase (for example, carrier for separation of biological substance and the like), they can be utilized as an affinity moiety for selectively adsorbing microorganisms expressing mannose on surface layers, especially such viruses. If benzonaphthacene glycoside derivatives facilitating such use can be obtained, they will be useful for development of novel medicaments and novel diagnostic agents, further, development of novel techniques concerning differentiation, fusion and regeneration of cells, and development of means for separating microorganisms.

As for the above fault (ii) which is one of causes of the unsuccessful practical application of the benzonaphthacene glycosides so far, for example, the inventors of the present invention presumed that the unsuccessfulness of providing candidate compounds having improved solubility is attributable to the fact that, for obtaining mannose binding property, these compounds have requirements such as a) an appropriate arrangement (naturally occurring type) of an oxygen containing functional group binding to the benzonaphthacene structure (aglycon) is maintained, b) the amino acid forming the amino acid side chain is glycine or a D-amino acid, c) the first saccharide directly binding to the aglycon is a D-fucose type saccharide, which causes synthetic limitations of the derivatives.

On the basis of the aforementioned presumption, modification of the second saccharide that binds to the 3-position of the aforementioned fucose type saccharide, and D-xylose, if present, was examined. As a result, it was unexpectedly found that when a product obtained from, for example, the Malaprade-type oxidative degradation of the second saccharide and D-xylose, if present, was further oxidized and thereby converted to have carboxyl group, derivatives were successfully obtained which had reduced self-aggregational property compared to the prior compounds, whilst still had desired mannose binding property, and moreover, had significantly improved solubility in aqueous media. Furthermore, one of the carboxyl groups provided as described above is a primary carboxyl group, and has preferential reactivity than the secondary carboxyl group that may exist in the D-amino acid moiety as the other carboxyl group. Therefore, to the product obtained by the aforementioned oxidation reaction, various groups or residues of compounds can be covalently bonded via the primary carboxyl group, and via a linker as required. It was also found that the conjugate obtained as described above still had the specific binding property to mannan (especially terminal D-mannose) expressed on cell surface layers.

The present invention thus provides a compound represented by the following general formula (A) or a salt thereof. Further, as described above, the compound represented by the following general formula (A) has a specific binding property to a microorganism expressing a mannose sugar chain. The compound was confirmed to be usable as raw materials for extensive purposes utilizing the aforementioned feature.

General Formula (A)

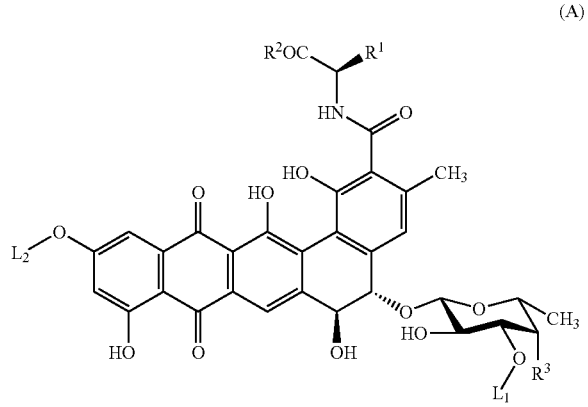

In the formula:
$R^1$ represents hydrogen atom, methyl, or hydroxymethyl,
$R^2$ represents hydroxy, amino, or mono- or di-$C_1$-$C_6$ alkyl-substituted amino,
$R^3$ represents hydroxy, amino, monomethylamino, or dimethylamino,
$L_1$ represents a group represented by the formula (B):

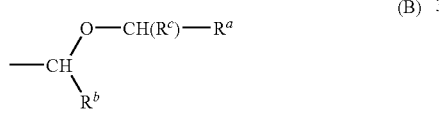

wherein $R^a$ and $R^b$ represent carboxyl, $R^c$ represents hydrogen atom or hydroxymethyl, or
when $R^3$ is amino or monomethylamino, $R^3$ and $R^b$ in $L_1$ combine together to represent a bridging group:

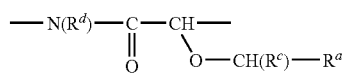

wherein $R^a$ and $R^c$ have the same meanings as defined above, and $R^d$ represents hydrogen atom or methyl, and
$L_2$ represents hydrogen atom, methyl, or a group represented by the formula (C):

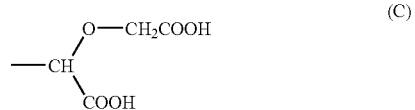

According to a preferred embodiment of the present invention, there is provided the aforementioned compound, wherein $R^2$ in the general formula (A) is hydroxy, $R^3$ is monomethylamino or dimethylamino, $L_1$ is a group represented by the formula (B), and $R^c$ is hydrogen atom.

The compound represented by the aforementioned general formula (1) can be used in the technical fields where the characteristic feature of specific binding to a microorganism expressing a mannose sugar chain, for example, fungi, viruses, certain types of animal, and plant cells (including insect cells). For example, the compound can be used as a raw material for preparing antifungal agents, therapeutic agents such as anti-HIV agents, and affinity moieties of carriers for selective adsorption of microorganisms expressing a mannose sugar chain. In particular, the compound of the present invention has high water solubility and reduced self-aggregationnal property, and accordingly, highly purified compound without containing impurities can be easily provided, thereby a therapeutic agent having reduced side effect and superior kinetics in vivo can be provided.

DETAILED DESCRIPTION OF THE INVENTION

The present invention will be explained in detail.
In the compound represented by the general formula (A) according to the present invention, each moieties other than the groups $L_1$ and $L^2$ has configuration as shown in the formula, which is the same configuration as that of the moieties of antibiotics pradimicin (henceforth also abbreviated as "PRM") and benanomicin (henceforth also abbreviated as "BNM") isolated from the culture of rare aotinomycetes, other than the second saccharide residue (i.e., D-xylose or D-glucose) in the sugar chains thereof.

Therefore, the amino acid side chain of the compound of the general formula (A) consists of glycine residue or a D-amino acid residue, i.e., consists of a D-alanine residue when $R^1$ is methyl, and consists of a D-serine residue when $R^1$ is hydroxymethyl. In PRM obtained from the aforementioned culture, the group corresponding to $R^2$ in the general formula (A) is hydroxy. However, $R^2$ of the compound of the present invention may be amino or a mono- or di-$C_1$-$C_6$ alkyl-substituted amino. The compound in which $R^2$ is a group other than hydroxy also has the binding ability to a surface layer of a cell expressing mannan having a D-mannose residue at the end, and the compound is preferred for providing a further derivative or conjugate utilizing the primary carboxyl in the groups $L_1$ and/or $L_2$. When the further modification (derivatization) via the groups $L_1$ and/or $L_2$ is not performed, $R^2$ is preferably hydroxy.

The $C_1$-$C_6$ alkyl group means a branched or straight alkyl group having 1 to 6 carbon atoms, and examples include, for example, methyl, ethyl, n-propyl, isopropyl, n-butyl, sec-butyl and n-hexyl.

$R^3$ may be amino or monomethylamino in the same manner as the corresponding group in, for example, PRM C and PRM A, or may be hydroxy in the same manner as the corresponding group in BNM A.

Further, $R^3$ may be dimethylamino in the same manner as the corresponding group in BMY-28864.

A specific example of the group represented by the formula (3) as $L^1$ is either of the following groups depending on whether the second saccharide in the sugar chain of the starting material for obtaining the compound represented by the formula (A) is D-xylose or D-glucose.

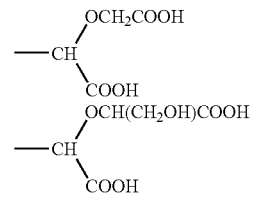

When $R^3$ is amino or monomethylamino, $R^3$ together with the aforementioned $L_1$ may represent a bridging group:

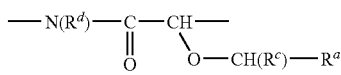

wherein $R^a$ represents carboxyl, $R^c$ represents hydrogen atom or hydroxymethyl, and $R^d$ represents hydrogen atom or methyl. $R^3$ and $L_1$ representing this kind of bridging group form a ring structure:

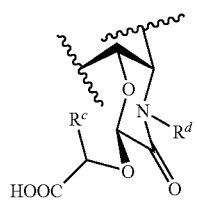

together with the carbon-carbon bond of the fucose type saccharide residue to which they bond.

The compound represented by the aforementioned general formula (A) may be a salt of carboxylic acid with an inorganic or organic base. Example of inorganic base that can form such salt include hydroxides of alkali metals (Na, K, Li and the like) or alkaline earth metals (Mg, Ca and the like), and carbonic acid salts, and example of organic base include ethanolamine, diethanolamine, and the like. The compound or a salt thereof exhibits a biological activity similar to those of PRM antibiotics, and is useful as a therapeutic agent.

Furthermore, the compound represented by the general formula (A) can be used to provide conjugates in which various compounds are covalently bound to the compound represented by the general formula (A) via the primary carboxyl existing in the groups $L_1$ and/or $L_2$, and further by means of a linker, as required. Examples of the linker include, but not limited to, an α,ω-alkylenediamine (the alkylene is, for example, a $C_2$-$C_{20}$ alkylene, and may be interrupted with two or more imino (—NH—) or oxy (—O—) groups). Although the compounds for forming the conjugates are not limited, examples include compounds that can make the compound of the general formula (A) into a prodrug, for example, pivaloyloxymethyl halides and lower alkyl halides. Halides and esterification products of the compound of the general formula (A) are useful as prodrugs. Further, the above compounds are expected to be absorbed from the intestinal tract as orally-administered agent due to high liposolubility, the compounds are expected to exert effectiveness as an active compound in blood after hydrolysis.

Examples of other compounds that can be covalently bound to the primary carboxyl, preferably by means of a linker, include anti-HIV agents, for example, nucleic acid type reverse transcriptase inhibitors such as 3'-azido-3'-deoxythymidine (AZT), 2',3'-dideoxyinosine (Videx), and 2',3'-dideoxycytidine (Hivid), non-nucleic acid type reverse transcriptase inhibitors such as nevirapine and Rescriptor, and protease inhibitors such as ritonavir, Norvir, Invirase and Crixivan. The aforementioned agents are bound to the carboxyl of the compound of the general formula (A) or a terminal functional group of the linker by utilizing a functional group such as hydroxy, amino, imino, carboxy or a halogen atom of the agents when the agents have such a functional group, or utilizing a moiety that carries such functional group introduced into the agents as required. The conjugate thus obtained, e.g., that of an anti-HIV agent and the compound of the general formula (A), will be able to selectively recognize cells infected by HIV and expressing mannose on surface layers and kill the cells.

As further conjugates, the conjugate may formed with a compound which can serve as a fluorescence source such as 7-amino-4-methylcoumarin, 4'-(aminomethyl)fluorescein, and 4-(9-anthroyloxy)phenacyl bromide. For obtaining such conjugate, if necessary, a modified compound may be used in which a compound which can serve as a fluorescence source is introduced with any one of the aforementioned functional groups. This type of conjugate can be useful as a tool for detecting fungi, viruses, HIV-infected cells and the like that express mannose on a surface layer. As described above, the compound represented by the general formula (A) can be used as a drug delivery carrier for a wide variety of medicaments targeting cells expressing a mannose sugar chain.

In addition, the compound immobilized on a surface of a water-insoluble solid phase support by means of the aforementioned primary carboxyl, preferably via a linker, is useful as a raw material for preparation of a separation carrier by affinity adsorption of microorganisms such as fungi and viruses expressing a mannose sugar chain. Examples of the water-insoluble solid phase support include carriers for column chromatography known per se, such as gels of various polysaccharides and other synthesized polymers and gels modified by introducing such functional groups as mentioned above on the surfaces as required.

The compound represented by the general formula (A) can be conveniently prepared by using PRM or BNM antibiotics described in Non-patent document 1 mentioned above and many references cited therein or Non-patent documents 3 and 4, or semi-synthesized derivatives obtainable therefrom as a starting material and by applying a step of oxidative degradation of the second saccharide moiety of the sugar chain. Such preparation can be performed according to, but not limited to, the following reaction schemes.

In the following reaction schemes, the following moiety of the general formula (A) is represented by an abbreviation $Z^-$.

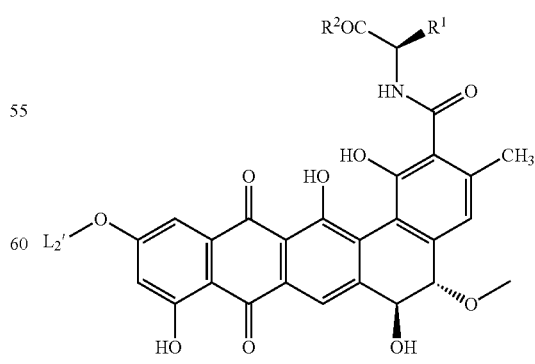

($L_2$' represents hydrogen atom, methyl, or D-xylose residue)

Reaction scheme 1
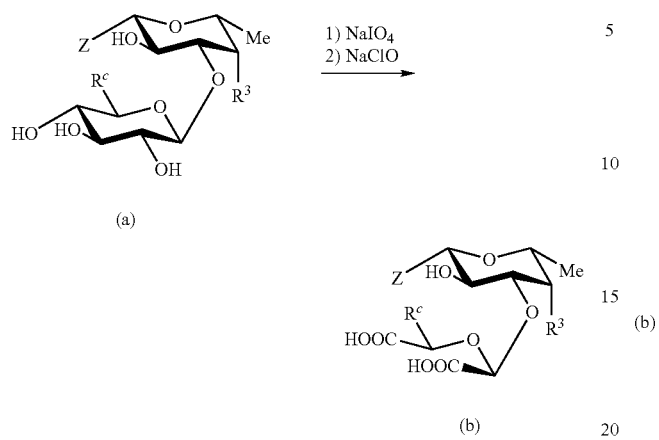
Reaction scheme 2
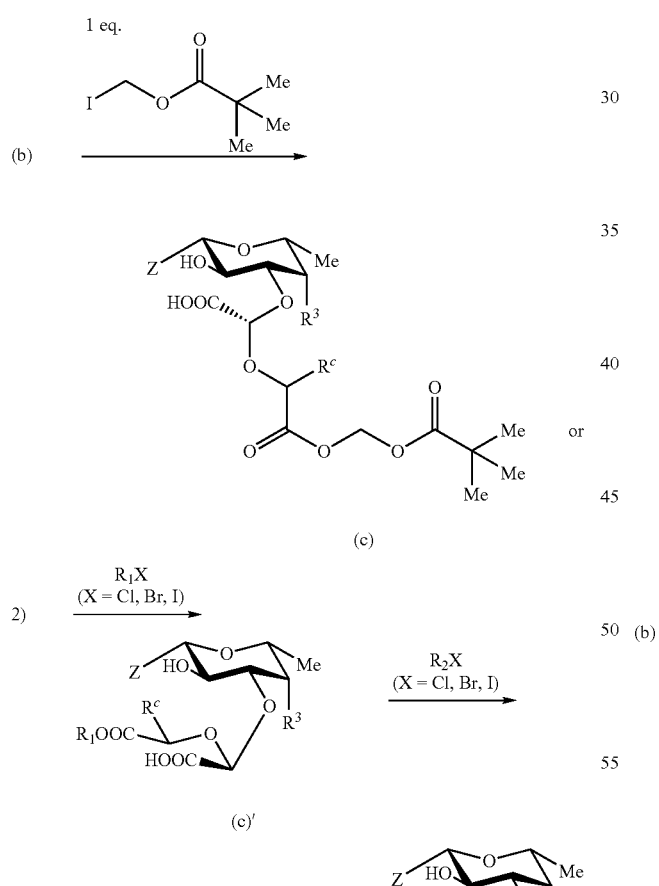
Reaction scheme 3
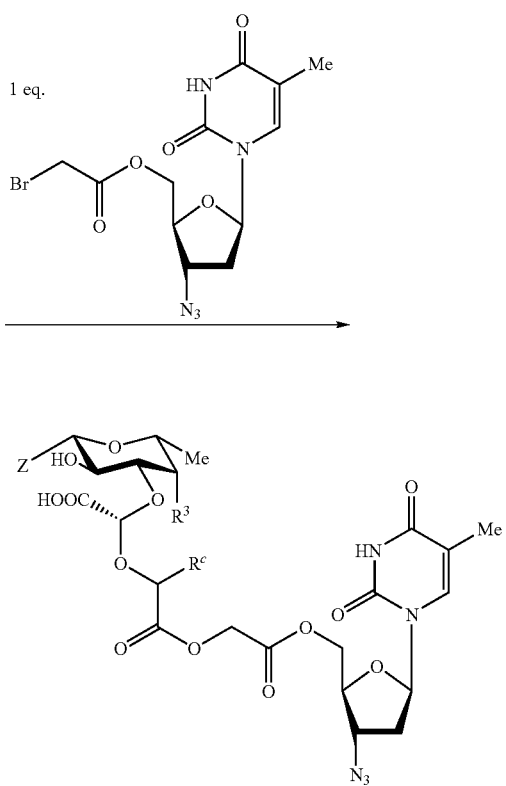
Reaction scheme 4
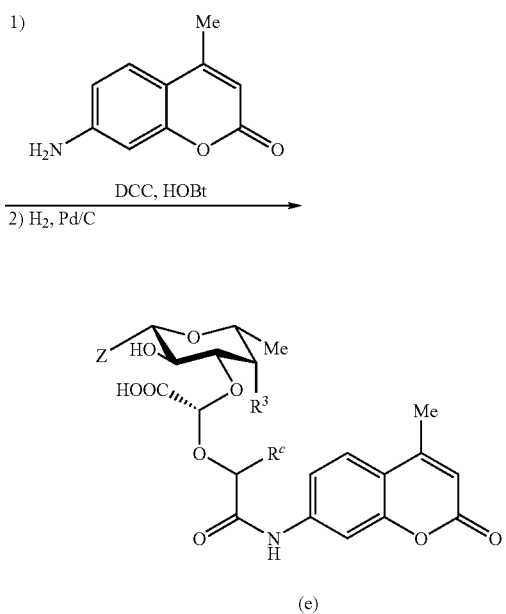

Reaction scheme 5

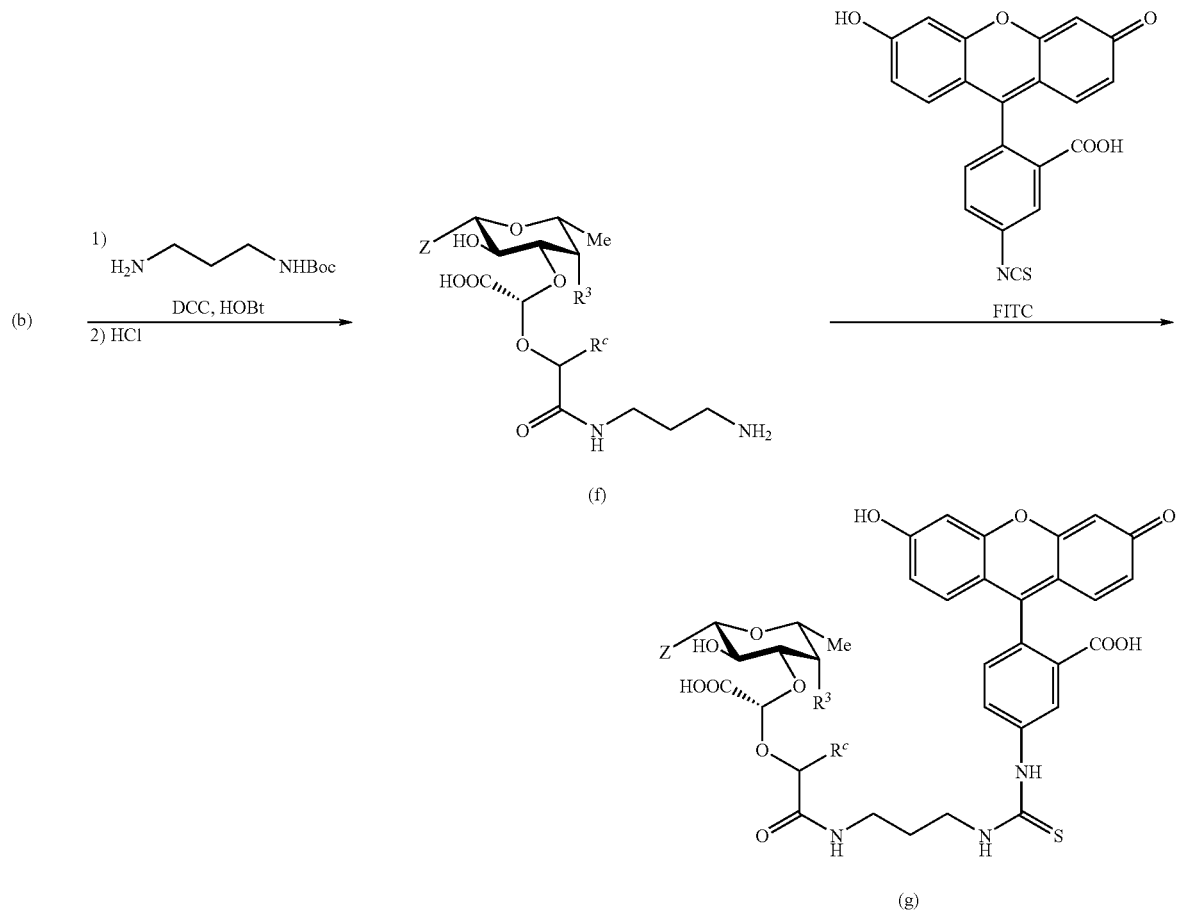

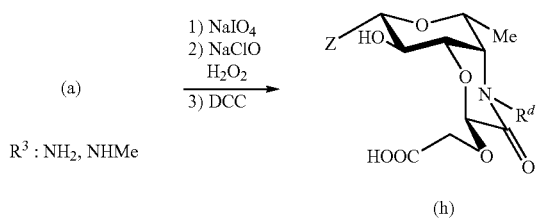

Reaction scheme 6

In the aforementioned formulas, $R^1$, $R^2$, $R^3$, $R^c$ and $R^d$ have the same meanings as defined above.

The starting material, Compound (a), can be prepared by the methods described in Non-patent documents 1 to 4, or when Compound (a) is a compound wherein $R^2$ is amino or a lower alkyl-substituted amino, the compound can be prepared by the method described in EP388982A1 or methods similar to the methods described in the aforementioned publications.

Reaction scheme 1 shows a conversion reaction from Compound (a) to Compound (b) concerning preparation of the key compound according to the present invention. This reaction can be performed by dissolving Compound (a) (when the compound contains amino or methyl-substituted amino as $R^3$, an acid addition salt thereof) in a mixed solvent of water with, for example, dimethyl sulfoxide (DMSO) and subjecting the solution to oxidation degradation using sodium periodate or the like at room temperature and further to an oxidation reaction. When $L_2'$ in Z is D-xylose residue, $L_2'$ is also oxidized, and converted into a group represented by the formula (C).

Reaction scheme 2 shows an example of preparation of a prodrug with Compound (b). The desired compound, i.e., Compound (c), can be prepared by dissolving Compound (b) in anhydrous dimethylformamide (DMF), then adding, for example, pivaloyloxymethyl iodide and potassium fluoride to the solution, and stirring the mixture at room temperature for 10 to 20 hours. Compound (c) can be obtained by diluting the reaction mixture, and then subjecting the diluted mixture to a desalting treatment using a DIAION HP-20 column or the like and a treatment using a reverse phase column or the like. Although Compound (a) also have one or two of secondary carboxyl groups, the primary carboxyl can generally be esterified with good selectivity. If the secondary carboxyl is also esterified, the desired ester can be separated by performing an ion exchange column treatment or the aforementioned reverse phase ODS column treatment. In addition, by repeating the aforementioned reactions with a halide other than pivaloyloxymethyl iodide mentioned above (with warming, if necessary), the remaining carboxyl may also be converted into ester.

Reaction scheme 3 shows an example of preparation of a conjugate for drug delivery of an anti-HIV agent. For example, 3'-azido-3'-deoxythymidine (AZT) is dissolved in pyridine and methylene chloride, and acetyl bromide is added dropwise to the solution under cooling. After stirring for several tens of minutes, the reaction mixture is poured into ice water, and the product is extracted with ethyl acetate. 5-Bromoacetyl-AZT is thus prepared. This halide compound and potassium fluoride are added to an anhydrous DMF solution of Compound (a), and the mixture is stirred at room temperature for about 18 hours. Recovery of the desired product from the reaction mixture can be performed in the same manner as that applied in Reaction scheme 2 mentioned above.

Reaction scheme 4 shows a method of binding a fluorescence label to Compound (a). A benzyl ester of Compound (a) is prepared, and dissolved in anhydrous DMF, then, for example, 7-amino-4-methylcoumarin, N-hydroxybenzotriazole and DCC are added to the solution, and the mixture is stirred at room temperature for about 18 hours. The reaction mixture is diluted, then passed through, for example, a DIAION HP-20 column, and after desalting by washing with water, eluted with acetone/aqueous hydrochloric acid (pH 3), and the eluate is lyophilized. This product is dissolved in methanol and water, 5% Pd/C is added to the solution, and the mixture is stirred for 6 hours under a hydrogen atmosphere to perform debenzylation. The reaction mixture is filtered and concentrated under reduced pressure, and the residue is purified by using a reverse phase ODS column (eluent: acetonitrile/phosphate buffer, pH 3.5, gradient) to collect fractions containing the objective component. Compound (e) corresponding to the starting material is obtained from the eluate.

Reaction scheme 5 showns an example of introduction of a fluorescence label into Compound (a) by means of a spacer. Each of the amidation reactions and purification of the product can be performed in the same manner as that used in Reaction scheme 3 mentioned above.

Reaction scheme 6 shows an example of the preparation accompanied by a cyclization reaction of the oxidative degradation product of Compound (a). The desired compound (h) is obtained by subjecting Compound (a) to the same oxidation reaction as that of Reaction scheme 1 and subsequently condensing the product.

A desired compound or a desired conjugate can be obtained as described above, or by modification of the reactions of the aforementioned reaction schemes, if necessary. Although Compound (b) may sometimes have an antifungal activity slightly less than that of the PRM antibiotics as the starting materials, however, water solubility thereof is significantly improved.

The present invention will be explained with reference to specific examples. However, the present invention is not limited to these examples.

EXAMPLE 1

Preparation of dicarboxylic Acid of PRM A
(Henceforth Abbreviated as PRM A-DCA)

Pradimicin (PRM) A hydrochloride (50 mg, 0.06 mmol) was dissolved in a mixed solvent of DMSO (2 ml) and distilled water (8 ml), and sodium periodate (100 mg) was added to the solution at room temperature with stirring. Although the reaction mixture slightly generated heat, the mixture was left being continually stirred for 3 hours. The reaction mixture was adjusted to pH 4.1 to 4.5 with a diluted sodium hydroxide solution, then successively added with 80% sodium chlorite (13 mg, 0.12 mmol), 35% aqueous hydrogen peroxide (15 µl, 0.12 mmol) and aqueous sodium dihydrogenphosphate dihydrate (2 g, 10 ml), and stirred at room temperature for 1 hour. The reaction mixture was added with sodium thiosulfate pentahydrate (11.4 mg), and further stirred for 1 hour. Then, the reaction mixture was passed through a DIAION HP-20 column, and after desalting by washing with water, eluted with acetone/aqueous hydrochloric acid (pH 3), and the eluate was concentrated to dryness. The resulting crude reaction product was purified by using a reverse phase ODS column (eluent: acetonitrile/phosphate buffer, pH 3.5, gradient), and fractions containing the desired compound were collected. Acetonitrile was evaporated from the eluate by using an evaporator, and the resulting solution was subjected to desalting and then elution with acetone/aqueous hydrochloric acid (pH 3) in a HP-20 column. Acetone was evaporated under reduced pressure from the eluate, and the resulting aqueous solution was lyophilized to obtain PRM A-DCA (31 mg, yield: 62%).

By using N,N-Me$_2$-PRM C (pradimioin C of which R$^3$ was dimethylated) and BMY28864 (mentioned above) as starting materials instead of PRM A, the corresponding compounds, N-Me$_2$-PRMC-DCA and MY28864-DCA, were obtained, respectively.

EXAMPLE 2

Tests for Observing Characteristic Features

1) Solubility Test

PBS tablets (ICN Bioohemi Inc., containing 0.02 g of KH$_2$PO$_4$, 0.115 g of Na$_2$HPO$_4$, 0.02 g of KCl and 10.8 g of NaCl per tablet) were dissolved in distilled water (100 ml), and the solution was autoclaved to obtain a PBS(−) solution. The PBS(−) solution (80 ml) was added with CaCl$_2$ dihydrate (1 g/L, 10 ml) and MgCl$_2$ hexahydrate (1 g/L, 10 ml) to prepare a PBS(+) solution.

Each test compound (1 mg) was added to the PBS(−) solution (300 µl), and the mixture was ultrasonicated at 30° C. for 10 minutes, and left at room temperature for 2 hours. Then, the mixture was centrifuged (12,000 rpm, 10 minutes), the supernatant was diluted 50 times with 0.01 N sodium hydroxide solution, and absorbance of the diluted mixture was measured at 500 nm. The amount of the dissolved compound was calculated on the basis of $E_{1\ cm}^{1\%} 180$ (500 nm), and the solubility was calculated.

The solubility in the PBS(+) solution can also be obtained in a similar manner. The results are shown in Table 1 below.

TABLE 1

| | Solubility (µg/ml) | |
|---|---|---|
| Compound | PBS (−) | PBS(+) |
| PRM A | 39.5 | 68.5 |
| BMY28864 | 14,000 | 16,000 |
| N,N-Me$_2$-PRM C | 1,900 | 950 |
| PRM A-DCA | 2,250 | 2,300 |
| BMY28864-DCA | 37,500 | 37,500 |
| N,N-Me$_2$-PRM C-DCA | 1,400 | 1,850 |

2) Mannan Binding Test

A PBS(+) solution (100 µl) of mannan (Sigma, derived from yeast, 50 µg/ml) and a PBS(+) solution (100 µl) of each test compound (40 µg/ml) were mixed, and incubated at 30° C. for 24 hours. Then, the mixture was centrifuged (14,000 rpm, 4° C., 5 minutes), the supernatant was diluted 10 times with 0.01 N sodium hydroxide solution, and absorbance of the diluted mixture was measured at 500 nm. The amount of the dissolved compound was calculated on the basis of $E_{1\ cm}^{1\%}180$ (500 nm), and the amount of the compound binding to mannan was calculated. The results are shown in Table 2 below.

TABLE 2

Mannan binding property

| Compound | Binding to mannan [µg/1 µg of mannan] |
|---|---|
| PRM A | 0.89 |
| BMY28864 | 0.81 |
| N,N-Me$_2$-PRM C | 0.79 |
| PRM A-DCA | 0.02 |
| BMY28864-DCA | 0.28 |
| N,N-Me$_2$-PRM C-DCA | ~0 |

~0: Below detection limit (trace)
Incubation at 30° C. for 24 hours

3) Antifungal Activity Test

Antifungal activity was measured by the agar dilution method utilizing the yeast morphology agar (0.15 M phosphate buffer, pH 7.0). Each microorganism was inoculated in an amount of 5 µl of 2×10$^6$ cells/ml solution per spot, and cultured at 30° C. for 2 days. The results were represented in terms of the minimum growth inhibitory concentration. As a control compound, BMY28864 was used. It was revealed that N,N-Me$_2$-PRM C-DCA exhibited the strongest activity among the three kinds of DCA derivatives, and although the activity thereof against *A. fumigatus* was lower than that of BMY28884, the activities against *C. albicans* and *C. neoformans* were almost equal to those of BMY28884. Further, activities of PRM A-DCA and BMY28864-DCA against *A. fumigatus* were relatively low, whilst the activities thereof against *C. albicans* and *C. neoformans* were maintained. These results demonstrate that the PRMC-DCA derivatives are active derivatives.

TABLE 3

Antifungal activity

| | MIC (µg/ml) | | |
|---|---|---|---|
| Compound | *C. albicans* A9540 | *A. fumigatus* IFO8866 | *C. neoformans* ATCC 90112 |
| BMY28864 | 6.3 | 12.5 | 3.1 |
| PRM A-DCA | 6.3 | >50 | 12.5 |
| N,N-Me$_2$-PRM C-DCA | 6.3 | 25 | 3.1 |
| BMY28864-DCA | 12.5 | >50 | 25 |

From the results mentioned above, it was revealed that the solubility of the compounds of the present invention was significantly improved compared with the known compounds (see, Table 1), and the mannan sugar chain binding ability of the same was reduced (see, Table 2), from which reduction of the agglutination property is presumed, whilst they had strong antifungal activity (see, Table 3).

EXAMPLE 3

Synthesis of methyl ester Derivative of BMY28864-OCA (Henceforth Referred to as BMY28864-DCA-TEMe)

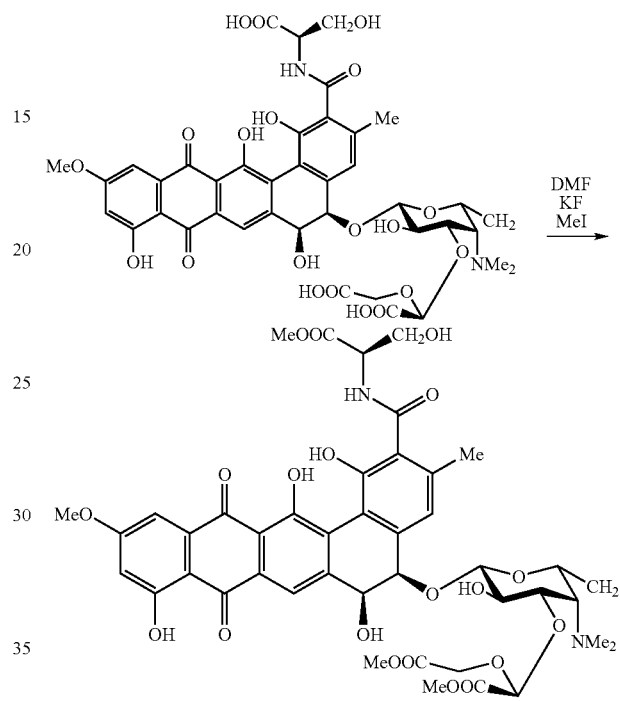

BMY28864-DCA (30 mg, 0.034 mmol) was dissolved in DMF (3 ml), and added with KF (30 mg, 0.516 mmol) and MeI (5 ml), and the mixture was stirred overnight. During this operation, the reaction mixture was shielded from light with aluminum foil, since MeI is unstable to light. Then, the reaction mixture was diluted by addition of a substantially equal volume of distilled water, passed through a DIAION HP-20 column, desalted by washing with water, and then eluted with acetone/aqueous hydrochloric acid (pH 3), and the eluate was concentrated to dryness. The resulting crude reaction product was purified by using a reverse phase OPS column (eluent: acetonitrile/phosphate buffer, pH 3.5, gradient), and fractions containing the objective component were collected. Acetonitrile was evaporated form the eluate by using an evaporator, and the resulting solution was subjected to desalting and then elution with acetone/aqueous hydrochloric acid (pH 3) in a HP-20 column. Acetone was evaporated under reduced pressure from the eluate, and the resulting aqueous solution was lyophilized to obtain BMY28864-DCA-TEMe (5.1 mg, yield: 17.0%).

When the reaction was performed by using EtI, PrI or BuI instead of MeI as an electrophilic reagent, a triester compound corresponding to each compound was similarly obtained. The yields were 44.7% for TEEt, 27.0% for TEPr, and 40.3% for TEBu. Further, when the reaction was performed with MeI, the compound introduced with two of the esters was by-produced.

Further, when BMY28864-DCA-TEBu was synthesized, the triester and diester compounds as well as the monoester compound were simultaneously produced as in the reaction for the TEMe compound. When BuI was excessively added, all of the starting material, monoester, and diester were consumed, and the esterification advanced to production of triester.

Although the reaction product becomes complicated, monoester, diester and triester can be synthesized by controlling the amount of the alkyl halide.

What is claimed is:

1. A compound represented by the general formula (A) or a pharmaceutically acceptable salt thereof:

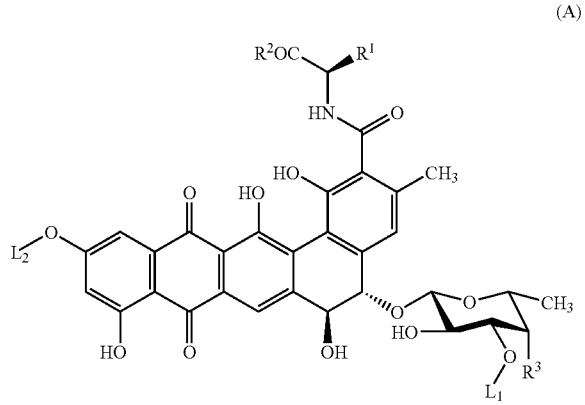

(A)

wherein:
$R^1$ represents hydrogen atom, methyl, or hydroxymethyl,
$R^2$ represents hydroxy, amino, or mono- or di-$C_1$-$C_6$ alkyl-substituted amino,
$R^3$ represents hydroxy, amino, monomethylamino, or dimethylamino,
$L^1$ represents a group represented by the formula (B):

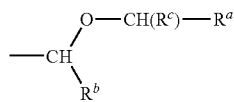

(B)

wherein $R^a$ and $R^b$ represent carboxyl, $R^c$ represents hydrogen atom or hydroxymethyl, or when $R^3$ is amino or monomethylamino, $R^3$ and $R^b$ in $L_1$ combine together to represent a bridging group:

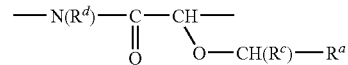

wherein $R^a$ and $R^c$ have the same meanings as defined above, and $R^d$ represents hydrogen atom or methyl, and
$L_2$ represents hydrogen atom, methyl or a group represented by the formula (C):

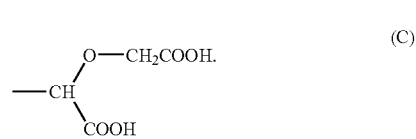

(C)

2. The compound according to claim 1, wherein $R^2$ is hydroxy, and $L_1$ is a group represented by the formula (B).

3. The compound according to claim 1, wherein $R^2$ is hydroxy, $L_1$ is a group represented by the formula (B), and $L_2$ is hydrogen atom or methyl.

4. The compound according to claim 1, wherein $R^2$ is hydroxy, $L_1$ is a group represented by the formula (B), and $L_2$ is a group represented by the formula (C).

5. The compound according to claim 1, wherein $R^2$ is hydroxy, $R^3$ is monomethylamino or dimethylamino, and $L_1$ is a group represented by the formula (B), wherein $R^c$ is hydrogen atom.

6. The compound according to claim 1, wherein $R^1$ is methyl, $R^2$ is hydroxy, $R^3$ is monomethylamino, $L_1$ is a group represented by the formula (B), wherein $R^a$ and $R^b$ are carboxyl groups, and $R^c$ is hydrogen atom, and $L_2$ is methyl.

7. The compound according to claim 1, wherein $R^1$ is methyl, $R^2$ is hydroxy, $R^3$ is dimethylamino, $L_1$ is a group represented by the formula (B), wherein $R^a$ and $R^b$ are carboxyl groups, and $R^c$ is hydrogen atom, and $L_2$ is methyl.

8. The compound according to claim 1, wherein $R^1$ is hydroxymethyl, $R^2$ is hydroxy, $R^3$ is dimethylamino, $L_1$ is a group represented by the formula (B), wherein $R^a$ and $R^b$ are carboxyl groups, and $R^c$ is hydrogen atom, and $L_2$ is methyl.

* * * * *